(12) United States Patent
Masuno et al.

(10) Patent No.: US 9,637,463 B2
(45) Date of Patent: May 2, 2017

(54) UTILIZING A MULTIPHASE REACTOR FOR THE CONVERSION OF BIOMASS TO PRODUCE SUBSTITUTED FURANS

(71) Applicant: MICROMIDAS, INC., West Sacramento, CA (US)

(72) Inventors: Makoto Nathanael Masuno, Elk Grove, CA (US); John Bissell, II, Sacramento, CA (US); Ryan L. Smith, Sacramento, CA (US); Brian Higgins, Davis, CA (US); Alex B. Wood, Sacramento, CA (US)

(73) Assignee: MICROMIDAS, INC., West Sacramento, CA (US)

( * ) Notice: Subject to any disclaimer, the term of this patent is extended or adjusted under 35 U.S.C. 154(b) by 0 days.

(21) Appl. No.: 14/805,321

(22) Filed: Jul. 21, 2015

(65) Prior Publication Data
US 2016/0168107 A1    Jun. 16, 2016

Related U.S. Application Data

(63) Continuation of application No. 14/124,240, filed as application No. PCT/US2012/041087 on Jun. 6, 2012, now Pat. No. 9,126,964.

(60) Provisional application No. 61/495,324, filed on Jun. 9, 2011.

(51) Int. Cl.
*C07D 307/46* (2006.01)
*C07D 307/50* (2006.01)

(52) U.S. Cl.
CPC ......... *C07D 307/50* (2013.01); *C07D 307/46* (2013.01)

(58) Field of Classification Search
CPC .............................. C07D 307/50; C07D 307/46
See application file for complete search history.

(56) References Cited

U.S. PATENT DOCUMENTS

| | | | | |
|---|---|---|---|---|
| 4,001,283 A * | 1/1977 | Wells, Jr. ............. | C07D 307/50 | 549/489 |
| 4,424,390 A | 1/1984 | Hamada et al. | | |
| 4,433,155 A | 2/1984 | Gilpin | | |
| 6,162,350 A | 12/2000 | Soled et al. | | |
| 7,173,142 B2 * | 2/2007 | Steiner ................. | C07D 307/50 | 549/489 |
| 7,829,732 B2 | 11/2010 | Mascal | | |
| 9,102,644 B2 | 8/2015 | Mikochik et al. | | |
| 9,126,964 B2 | 9/2015 | Masuno et al. | | |
| 2007/0161795 A1 | 7/2007 | Cvak et al. | | |
| 2010/0210745 A1 | 8/2010 | McDaniel et al. | | |
| 2014/0187802 A1 | 7/2014 | Mikochik et al. | | |
| 2015/0203462 A1 | 7/2015 | Cahana et al. | | |

FOREIGN PATENT DOCUMENTS

| | | |
|---|---|---|
| EP | 1049657 B1 | 3/2003 |
| GB | 1220851 A | 1/1971 |
| GB | 1448489 A | 9/1976 |
| WO | 96/38500 A1 | 12/1996 |
| WO | 99/25675 A1 | 5/1999 |
| WO | 2012/170520 A1 | 12/2012 |
| WO | 2013/024162 A1 | 2/2013 |

OTHER PUBLICATIONS

Alonso, D. M., "Catalytic conversion of biomass to biofuels." Green Chemistry 12.9 (2010): 1493-1513.*
BeMiller, J.N.,"Carbohydrates" Kirk-Othmer Encyclopedia of Chemical Technology. Copyright John Wiley & Sons, Inc., vol. 4. p. 696-733; published online Jan. 16, 2004.*
Kaliyan, N., "Densification characteristics of corn cobs." Fuel Processing Technology 91.5 (2010): 559-565.*
Jin, F.,"Application of hydrothermal reaction to conversion of plant-origin biomasses into acetic and lactic acids." Journal of Materials Science 43.7 (2008): 2463-2471.*
Werther, J.,"Fluidized-Bed Reactors." Ullmann's Encyclopedia of Industrial Chemistry 2007 p. 319-366.*
Intention to Grant received for European Patent Application No. 12733249.2, mailed on Aug. 21, 2015, 7 pages.
Notice of Allowance received for U.S. Appl. No. 14/438,600, mailed on Nov. 12, 2015, 6 pages.
Office Action received for Chinese Patent Application No. 201280028270.2, mailed on Oct. 10, 2015, 6 pages (3 pages of English Translation and 3 pages of Official Copy).
Brasholz et al., "Highly Efficient Dehydration of Carbohydrates to 5-(chloromethyl)Furfural(CMF), 5-(hydroxymethyl)Furfural (HMF) and Levulinic acid by Biphasic Continuous Flow Processing", Green Chemistry, vol. 13, 2011, pp. 1114-1117.
Breeden et al., "Microwave Heating for Rapid Conversion of Sugars and Polysaccharides to 5-Chloromethyl Furfural", Green Chemistry, vol. 15, 2013, pp. 72-75.
Chundury et al., "Preparation of Polymeric Building Blocks from 5-Hydroxymethyl- and 5-Chloromethylfurfuraldehyde", Industrial and Engineering Chemistry Product Research and Development, vol. 20, No. 1, 1981, pp. 158-163.
Horstman Fenton et al., "XLI-Bromomethylfurfuraldehyde", Journal of the Chemical Society, Transactions, vol. 75, 1899, pp. 423-433.
Haworth et al., "The Conversion of Sucrose into Furan Compounds. Part I. 5-Hydroxymethylfurfuraldehyde and some derivatives", Journal of the Chemical Society, 1944, pp. 667-670.
Hibbert et al., "Studies on Cellulose Chemistry II. The Action of dry Hydrogen Bromide on Carbohydrates and Polysaccharides1,2", Journal of the American Chemical Society, vol. 45, No. 1, 1923, pp. 176-182.
Horstman Fenton et al., "LXXXV-Derivatives of Methylfurfural", Journal of the Chemical Society, Transactions, vol. 79, 1901, pp. 807-816.
Kumari et al., "Synthesis of 5-Bromomethylfurfural from Cellulose as a Potential Intermediate for Biofuel", European Journal of Organic Chemistry, vol. 2011, 2011, pp. 1266-1270.

(Continued)

*Primary Examiner* — Samantha Shterengarts
*Assistant Examiner* — Matt Mauro
(74) *Attorney, Agent, or Firm* — Morrison & Foerster LLP

(57) ABSTRACT

The present disclosure provides methods to produce substituted furans (e.g., halomethylfurfural, hydroxymethylfurfural, and furfural), by acid-catalyzed conversion of biomass using a gaseous acid in a multiphase reactor, such as a fluidized bed reactor.

40 Claims, 1 Drawing Sheet

(56) References Cited

OTHER PUBLICATIONS

Liu et al., "Theoretical Studies on Thermochemistry for Conversion of 5-Chloromethylfurfural into Valuable Chemicals", The Journal of Physical Chemistry A., vol. 115, No. 46, 2011, pp. 13628-13641.
Mascal et al., "Dramatic Advancements in the Saccharide to 5-(Chloromethyl)furfural Conversion Reaction", Chemsuschem, vol. 2, No. 9, Sep. 21, 2009, pp. 859-861.
Moye, C. J., "5-Hydroxymethylfurfural", Reviews of Pure and Applied Chemistry, vol. 14, Jan. 1964, pp. 161-170.
Nawale et al., "Synthesis and Evaluation of Novel Thiazolidinedione Derivatives for Antibacterial Activity", Der Pharma Chemica, vol. 4, No. 6, 2012, pp. 2270-2277.
International Preliminary Report on Patentability received for PCT Patent Application No. PCT/US2013/066788, mailed on May 7, 2015, 9 pages.
International Search Report and Written Opinion received for PCT Patent Application No. PCT/US2013/066788, mailed on Feb. 6, 2014, 11 pages.
International Search Report and Written Opinion received for PCT Patent Application No. PCT/US2014/024940, mailed on Jul. 14, 2014, 12 pages.
International Preliminary Report on Patentability received for PCT Patent Application No. PCT/US2014/024949, mailed on Sep. 24, 2015, 15 pages.
International Search Report and Written Opinion received for PCT Patent Application No. PCT/US2014/024949, mailed on Jul. 11, 2014, 17 pages.
International Search Report & Written Opinion received for PCT Patent Application No. PCT/US2014/056572, mailed on Nov. 24, 2014, 9 pages.
Quiroz-Florentino et al., "Total Synthesis of Naturally Occurring Furan Compounds 5-{[(4-Hydroxybenzyl)oxy]methyl}-2-Furaldehyde and Pichiafuran C", Synthesis, vol. 7, pp. 1106-1112.
Sanda et al, "The Vilsmeier Reaction: A New Synthetic Method for 5-(Chloromethyl)-2-furaldehyde", Synthesis, No. 6, 1992, pp. 541-542.
Surh et al., "5-Sulfooxymethylfurfural as a possible ultimate Mutagenic and Carcinogenic Metabolite of the Maillard reaction Product, 5-Hydroxymethylfurfural", Carcinogenesis, vol. 15, No. 10, 1994, pp. 2375-2377.
Surh et al., "Activation of the Maillard Reaction Product 5-(Hydroxymethyl)furfural to Strong Mutagens via Allylic Sulfonation and Chlorination", Chemical Research in Toxicology, vol. 7, 1994, pp. 313-318.
Szmant et al., "The preparation preparation of 5-chloromethylfurfuraldehyde from high Fructose Corn Syrup and other Carbohydrates", Journal of Chemical Technology and Biotechnology, vol. 31, No. 1, 1981, pp. 205-212.
Timko et al., "The Furanyl Unit in Host Compounds", Journal of the American Chemical Society, vol. 96, No. 22, 1974, pp. 7159-7160.
Worden, Edward Chauncey, "Technology of Cellulose Esters", vol. 1, Part 1, 1921, p. 186.

* cited by examiner

US 9,637,463 B2

UTILIZING A MULTIPHASE REACTOR FOR THE CONVERSION OF BIOMASS TO PRODUCE SUBSTITUTED FURANS

CROSS-REFERENCE TO RELATED APPLICATIONS

This application is a Continuation of U.S. patent application Ser. No. 14/124,240, which is the U.S. National Stage Application of PCT/US2012/041087, filed internationally on Jun. 6, 2012, which claims priority to U.S. Provisional Patent Application No. 61/495,324 filed Jun. 9, 2011, all of which are incorporated herein by reference in their entireties.

FIELD

The present disclosure relates generally to the conversion of biomass into biofuels and chemicals. In particular, the present disclosure relates to the production of substituted furans (e.g., halomethylfurfural, hydroxymethylfurfural, and furfural) by acid-catalyzed conversion of biomass containing glycans (e.g., cellulose) and/or heteroglycans (e.g., hemicellulose), using a gaseous acid in a multiphase reactor.

BACKGROUND

Efforts to reduce dependence on fossil fuels for transportation fuel and as feedstock for industrial chemicals have been undertaken for decades, with a particular focus on enabling economic feasibility of renewable feedstock. Heightened efforts are being made to more effectively utilize renewable resources and develop "green" technologies, due to continued long-term increases in the price of fuel, increased environmental concerns, continued issues of geopolitical stability, and renewed concerns for the ultimate depletion of fossil fuels.

Conventional biofuel production from renewable feedstock employs a two-step process. In the first step, fermentable sugars are produced from biomass, typically by enzymatic saccharification. In the second step, the sugars are fermented into biofuels or chemicals. This two-step process, however, presents several technical challenges.

For example, biomass needs to be pretreated before hydrolysis can take place to produce sugars. Digestibility of cellulose in biomass is hindered by various physicochemical, structural and compositional factors. Pretreating biomass helps digest the cellulose and hemicellulose fractions of biomass by breaking down the lignin structure and disrupting the crystalline structures of cellulose and hemicellulose. This makes the biomass more accessible to hydrolysis for producing sugars used in subsequent fermentation. Common pretreatments known in the art involve, for example, mechanical treatment (e.g., shredding, pulverizing, grinding), concentrated acid, dilute acid, $SO_2$, alkali, hydrogen peroxide, wet-oxidation, steam explosion, ammonia fiber explosion (AFEX), supercritical $CO_2$ explosion, liquid hot water, and organic solvent treatments. These pretreatment options, however, are often expensive and technically difficult to implement on a commercial scale.

Moreover, acid conversion of biomass to produce the sugars often encounter mass transfer limitations that may reduce overall reaction yields and limit control of product selectivity. Grinding may improve mass transfer rates by reducing particle size; however, for solution-phase systems, the biomass particle size may be approximately one micron or less before mass transfer is no longer rate-limiting. Grinding biomass to this particle size may often be energy-intensive and commercially impractical.

Solution-phase hydrochloric acid (HCl)-catalyzed hydrolysis of cellulose may offer high glucose yields, but commercialization has been challenging. Technical considerations that may be expensive to address on a commercial scale include the high concentrations of aqueous HCl (≥40%) used for effective conversion and throughput under conditions of moderate temperature hydrolysis; high energy requirements for HCl recycling due to formation of boiling azeotropes of HCl and water at concentrations of 20 wt %; additional energy requirements to recover HCl solvent from the slurry cake formed from lignin that is saturated with HCl-rich solutions; and the use of large glass-lined reactors, which are often expensive, due to the high corrosiveness of HCl.

Once biomass is hydrolyzed to form sugars, challenges also exist to purify the resulting sugars and to remove hydrolysis by-products (e.g., acetate and formate). For example, if the cellulose used as a starting material is not pure, the sugars produced may be harder to isolate.

Substituted furans (e.g., halomethylfurfural, hydroxymethylfurfural, and furfural) produced from biomass may be converted into furanic derivatives used as biofuels and diesel additives, as well as a broad range of chemicals and plastic materials. For example, 5-(chloromethyl)furfural can be converted into 2,5-dimethylfuran, which may be used as a biofuel. Additionally, 5-(chloromethyl)furfural can be converted into 5-(ethoxymethyl)furfural, which is a combustible material that may be used as a diesel additive or kerosene-like fuel. Furanic derivatives, however, are currently under-utilized to produce chemical commodities because the commercial production methods are not economical.

The production of 5-(chloromethyl)furfural and 5-(hydroxymethyl)furfural from cellulose was first described in the early 1900s; however, slow kinetics and harsh reaction conditions make this method of biofuel production commercially unattractive.

What is needed in the art is a method to directly prepare biofuels and chemicals from biomass, thereby addressing some of the challenges associated with the conventional two-step process involving enzymatic saccharification and fermentation. What is also needed in the art is a method to prepare substituted furans (e.g., halomethylfurfural, hydroxymethylfurfural, and furfural) from biomass containing cellulose and/or hemicellulose in an efficient and cost-effective way. Once these substituted furans are produced, they can serves as intermediates that can be converted into to furanic derivatives such as biofuels, diesel additives, and plastics.

SUMMARY

The present disclosure addresses this need by providing processes to produce substituted furans (e.g., halomethylfurfural, hydroxymethylfurfural, and furfural) by acid-catalyzed conversion of biomass using a gaseous acid in a multiphase reactor. The processes disclosed herein make it possible to directly produce substituted furans (e.g., halomethylfurfural, hydroxymethylfurfural, and furfural) from the cellulose and/or hemicellulose in biomass in a way that minimizes the need for pretreating the biomass.

The present disclosure provides fast and cost-effective processes utilizing a multiphase reactor to convert a wide range of cellulosic feedstock into substituted furans (e.g., halomethylfurfural, hydroxymethylfurfural, and furfural). Other compounds, such as levulinic acid and formic acid, may also be produced by the processes. The processes employ a gaseous acid to catalyze the conversion of glycans (e.g., cellulose) and/or heteroglycans (e.g., hemicellulose) to substituted furans, such as hydroxymethylfurfural, chloromethylfurfural, and furfural—all within a single unit operation. Thus, the processes described herein open up an efficient industrial process to chemicals such as dimethylfuran, ethoxymethylfurfural, and furan dicarboxylic acid.

In one aspect, provided is a process for producing a substituted furan in a multiphase reactor, by: feeding biomass and a gaseous acid into a multiphase reactor; and mixing the biomass and the gaseous acid in the presence of a proton donor and a solvent to form a reaction mixture, under conditions suitable to produce a substituted furan, in which the reaction mixture has less than 10% by weight of water.

In some embodiments, the process further includes separating gaseous acid from the reaction mixture using a solid-gas separator; and drying the separated gaseous acid. The solid-gas separator may be a cyclone, a filter, or a gravimetric system.

In some embodiments that can be combined with the preceding embodiment, the process further includes feeding the dried gaseous acid into the multiphase reactor. In one embodiment, the multiphase reactor is a fluidized bed reactor.

In some embodiments that can be combined with any of the preceding embodiments, the gaseous acid is a halogen-based mineral acid or a halogen-based organic acid. In certain embodiments, the gaseous acid is gaseous hydrochloric acid. In other embodiments, the gaseous acid has less than 10% by weight of water. In one embodiment, the gaseous acid is dry. In certain embodiments, the gaseous acid is continuously fed into the multiphase reactor.

In some embodiments that can be combined with any of the preceding embodiments, the biomass includes glycans, heteroglycans, lignin, inorganic salts, cellular debris, or any combination thereof. In certain embodiments, the biomass is continuously fed into the multiphase reactor. In other embodiments, the biomass has less than 10% by weight of water.

In some embodiments that can be combined with any of the preceding embodiments, the proton donor is a Lewis acid. Suitable Lewis acids may include, for example, lithium chloride, sodium chloride, potassium chloride, magnesium chloride, calcium chloride, zinc chloride, aluminum chloride, boron chloride, or any combination thereof. In other embodiments, the proton donor has less than 10% by weight of water.

In some embodiments that can be combined with any of the preceding embodiments, the solvent is selected from dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, and any combination thereof. In some embodiments, the solvent is dry. In other embodiments, the solvent has less than 10% by weight of water.

In other embodiments that may be combined with any of the preceding embodiments, the pressure in the multiphase reactor is between 0.001 atm and 350 atm. In one embodiment, the pressure in the multiphase reactor is between 0.001 atm and 100 atm. In another embodiment, the pressure in the multiphase reactor is between 0.001 atm and 10 atm. In yet another embodiment, the pressure in the multiphase reactor is between 1 atm and 50 atm. In yet other embodiments that may be combined with any of the preceding embodiments, the temperature in the multiphase reactor is between 50° C. and 500° C. In one embodiment, the temperature in the multiphase reactor is between 100° C. and 400° C. In another embodiment, the temperature in the multiphase reactor is between 100° C. and 350° C. In yet another embodiment, the temperature in the multiphase reactor is between 150° C. and 300° C. In yet another embodiment, the temperature in the multiphase reactor is between 200° C. and 250° C.

In some embodiments that may be combined with any of the preceding embodiments, the substituted furan may include halomethylfurfural, hydroxymethylfurfural, furfural, or any combination thereof. In certain embodiments, the substituted furan is halomethylfurfural. In certain embodiments, the substituted furan is hydroxymethylfurfural. In certain embodiments, the substituted furan is furfural. In some embodiments, the halomethylfurfural is chloromethylfurfural, iodomethylfurfural, bromomethylfurfural, or fluoromethylfurfural. In one embodiment, the halomethylfurfural is chloromethylfurfural. In other embodiments, the halomethylfurfural is 5-(chloromethyl)furfural, 5-(iodomethyl)furfural, 5-(bromomethyl)furfural, or 5-(fluoromethyl)furfural. In another embodiment, the halomethylfurfural is 5-(chloromethyl)furfural. In some embodiments that may be combined with any of the preceding embodiments, the reaction mixture further includes levulinic acid, formic acid, alkylfurfural, or any combination thereof. In certain embodiments, the reaction mixture includes levulinic acid. In certain embodiments, the reaction mixture includes formic acid. In certain embodiments, the reaction mixture includes alkylfurfural. In certain embodiments, the alkylfurfural may be optionally substituted. In one embodiment, the alkylfurfural is methylfurfural.

Another aspect of the disclosure provides a process for producing a substituted furan in a multiphase reactor by: feeding biomass into a multiphase reactor; feeding a gaseous acid into the multiphase reactor, in which the gaseous acid has less than about 10% by weight of water; and mixing the biomass and the gaseous acid to form a reaction mixture that includes a substituted furan. In one embodiment, the process further includes separating gaseous acid from the reaction mixture using a solid-gas separator, and drying the separated gaseous acid. The solid-gas separator may be a cyclone, a filter, or a gravimetric system. In another embodiment that may be combined with any of the preceding embodiments, the process further includes feeding the dried gaseous acid into the multiphase reactor. This recycles the gaseous acid used in the process to produce the crude mixture.

In some embodiments that can be combined with any of the preceding embodiments, the process further includes adding a proton donor to the reaction mixture. In certain embodiments, the proton donor is a Lewis acid. Suitable Lewis acids may include, for example, lithium chloride, sodium chloride, potassium chloride, magnesium chloride, calcium chloride, zinc chloride, aluminum chloride, boron chloride, or any combination thereof. In other embodiments, the proton donor has less than 10% by weight of water.

In other embodiments that may be combined with any of the preceding embodiments, the process further includes combining the reaction mixture with a solvent, in which the solvent solubilizes the substituted furan, and in which the combining produces a solution that includes the substituted furan; and separating the solution. The solvent may include dichloromethane, ethyl acetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, or any combination thereof. In some embodiments that may be combined with any of the preceding embodiments, the solvent is dichloromethane, ethyl acetate, supercritical carbon dioxide, or any combination thereof. In some embodiments, the solvent is dry. In other embodiments, the solvent has less than 10% by weight of water.

In some embodiments that may be combined with any of the preceding embodiments, the solution may be separated from residual solids using a filter or a membrane system. In yet other embodiments that may be combined with any of the preceding embodiments, the process further includes distilling the solution to obtain the substituted furan. This distillation also produces a separated solvent. In some embodiments that may be combined with any of the preceding embodiments, the process further includes combining the separated solvent with a second reaction mixture. As such, the solvent may be recaptured.

In one embodiment that may be combined with any of the preceding embodiments, the multiphase reactor is a fluidized bed reactor. In some embodiments that may be combined with any of the preceding embodiments, the gaseous acid is a halogen-based mineral acid or a halogen-based organic acid. In certain embodiments, the gaseous halogen-based mineral acid is hydrochloric acid (HCl), hydroiodic acid (HI), hydrobromic acid (HBr), or hydrofluoric acid (HF). In one embodiment, the gaseous halogen-based mineral acid is hydrochloric acid (HCl). In some embodiments that may be combined with any of the preceding embodiments, the gaseous acid is continuously fed into the multiphase reactor.

In other embodiments that may be combined with any of the preceding embodiments, the biomass includes glycans, heteroglycans, lignin, inorganic salts, cellular debris, or any combination thereof. Particulates may also be present in the biomass, including for example clay, silica, humic materials, or any combination thereof. In yet another embodiment that may be combined with any of the preceding embodiments, the biomass is continuously fed into the multiphase reactor. In other embodiments, the biomass has less than 10% by weight of water.

In other embodiments that may be combined with any of the preceding embodiments, the pressure in the multiphase reactor is between 0.001 atm and 350 atm. In one embodiment, the pressure in the multiphase reactor is between 0.001 atm and 100 atm. In another embodiment, the pressure in the multiphase reactor is between 0.001 atm and 10 atm. In yet another embodiment, the pressure in the multiphase reactor is between 1 atm and 50 atm. In yet other embodiments that may be combined with any of the preceding embodiments, the temperature in the multiphase reactor is between 50° C. and 500° C. In one embodiment, the temperature in the multiphase reactor is between 100° C. and 400° C. In another embodiment, the temperature in the multiphase reactor is between 100° C. and 350° C. In yet another embodiment, the temperature in the multiphase reactor is between 150° C. and 300° C. In yet another embodiment, the temperature in the multiphase reactor is between 200° C. and 250° C.

In some embodiments that may be combined with any of the preceding embodiments, the substituted furan may include halomethylfurfural, hydroxymethylfurfural, furfural, and any combination thereof. In certain embodiments, the substituted furan is halomethylfurfural. In certain embodiments, the substituted furan is hydroxymethylfurfural. In certain embodiments, the substituted furan is furfural. In some embodiments, the halomethylfurfural is chloromethylfurfural, iodomethylfurfural, bromomethylfurfural, or fluoromethylfurfural. In one embodiment, the halomethylfurfural is chloromethylfurfural. In other embodiments, the halomethylfurfural is 5-(chloromethyl)furfural, 5-(iodomethyl)furfural, 5-(bromomethyl)furfural, or 5-(fluoromethyl)furfural. In another embodiment, the halomethylfurfural is 5-(chloromethyl)furfural. In some embodiments that may be combined with any of the preceding embodiments, the reaction mixture further includes levulinic acid, formic acid, alkylfurfural, or any combination thereof. In certain embodiments, the reaction mixture includes levulinic acid. In certain embodiments, the reaction mixture includes formic acid. In certain embodiments, the reaction mixture includes alkylfurfural. In certain embodiments, the alkylfurfural may be optionally substituted. In one embodiment, the alkylfurfural is methylfurfural.

Another aspect of the disclosure provides a process for producing halomethylfurfural, hydroxymethylfurfural, furfural, or any combination thereof in a multiphase reactor, by: feeding biomass into a multiphase reactor; feeding a gaseous acid into the multiphase reactor, in which the gaseous acid has less than about 10% by weight of water; and mixing the biomass and the gaseous acid to form a reaction mixture that includes halomethylfurfural, hydroxymethylfurfural, furfural, or any combination thereof. In one embodiment, the process further includes separating gaseous acid from the reaction mixture using a solid-gas separator, and drying the separated gaseous acid. The solid-gas separator may be a cyclone, a filter, or a gravimetric system. In another embodiment that may be combined with any of the preceding embodiments, the process further includes feeding the dried gaseous acid into the multiphase reactor. This recycles the gaseous acid used in the process to produce the crude mixture.

In some embodiments that can be combined with any of the preceding embodiments, the process further includes adding a proton donor to the reaction mixture. In certain embodiments, the proton donor is a Lewis acid. Suitable Lewis acids may include, for example, lithium chloride, sodium chloride, potassium chloride, magnesium chloride, calcium chloride, zinc chloride, aluminum chloride, boron chloride, or any combination thereof. In other embodiments, the Lewis acid has less than 10% by weight of water.

In other embodiments that may be combined with any of the preceding embodiments, the process further includes combining the reaction mixture with a solvent, in which the solvent solubilizes the halomethylfurfural, hydroxymethylfurfural, furfural, or any combination thereof, and in which the combining produces a solution that includes the halomethylfurfural, hydroxymethylfurfural, furfural, or any combination thereof; and separating the solution. The solvent may include dichloromethane, ethyl acetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, or any combination thereof. In some embodiments that may be combined with any of the preceding embodiments, the solvent is dichloromethane, ethyl acetate, supercritical carbon dioxide, or any combination thereof. In some embodiments, the solvent is dry. In other embodiments, the solvent has less than 10% by weight of water.

In some embodiments that may be combined with any of the preceding embodiments, the solution may be separated from residual solids using a filter or a membrane system. In yet other embodiments that may be combined with any of the preceding embodiments, the process further includes distilling the solution to obtain the halomethylfurfural, hydroxymethylfurfural, furfural, or any combination thereof. This distillation also produces a separated solvent. In some embodiments that may be combined with any of the preceding embodiments, the process further includes combining the separated solvent with a second reaction mixture. As such, the solvent may be recaptured.

In one embodiment that may be combined with any of the preceding embodiments, the multiphase reactor is a fluidized bed reactor. In some embodiments that may be combined with any of the preceding embodiments, the gaseous acid is a halogen-based mineral acid or a halogen-based organic acid. In certain embodiments, the gaseous halogen-based mineral acid is hydrochloric acid (HCl), hydroiodic acid (HI), hydrobromic acid (HBr), or hydrofluoric acid (HF). In one embodiment, the gaseous halogen-based mineral acid is hydrochloric acid (HCl). In some embodiments that may be combined with any of the preceding embodiments, the gaseous acid is continuously fed into the multiphase reactor.

In other embodiments that may be combined with any of the preceding embodiments, the biomass includes glycans, heteroglycans, lignin, inorganic salts, cellular debris, or any combination thereof. Particulates may also be present in the biomass, including for example clay, silica, humic materials, or any combination thereof. In yet another embodiment that may be combined with any of the preceding embodiments, the biomass is continuously fed into the multiphase reactor.

In other embodiments that may be combined with any of the preceding embodiments, the pressure in the multiphase reactor is between 0.001 atm and 350 atm. In one embodiment, the pressure in the multiphase reactor is between 0.001 atm and 100 atm. In another embodiment, the pressure in the multiphase reactor is between 0.001 atm and 10 atm. In yet another embodiment, the pressure in the multiphase reactor is between 1 atm and 50 atm. In yet other embodiments that may be combined with any of the preceding embodiments, the temperature in the multiphase reactor is between 50° C. and 500° C. In one embodiment, the temperature in the multiphase reactor is between 100° C. and 400° C. In another embodiment, the temperature in the multiphase reactor is between 100° C. and 350° C. In yet another embodiment, the temperature in the multiphase reactor is between 150° C. and 300° C. In yet another embodiment, the temperature in the multiphase reactor is between 200° C. and 250° C.

In some embodiments, the halomethylfurfural is chloromethylfurfural, iodomethylfurfural, bromomethylfurfural, or fluoromethylfurfural. In one embodiment, the halomethylfurfural is chloromethylfurfural. In other embodiments, the halomethylfurfural is 5-(chloromethyl)furfural, 5-(iodomethyl)furfural, 5-(bromomethyl)furfural, or 5-(fluoromethyl)furfural. In another embodiment, the halomethylfurfural is 5-(chloromethyl)furfural. In some embodiments that may be combined with any of the preceding embodiments, the reaction mixture further includes levulinic acid, formic acid, alkylfurfural, or any combination thereof. In certain embodiments, the alkylfurfural may be optionally substituted. In one embodiment, the alkylfurfural is methylfurfural.

BRIEF DESCRIPTION OF THE DRAWINGS

The present application can be best understood by reference to the following description taken in conjunction with the accompanying drawing figures, in which like parts may be referred to by like numerals.

DETAILED DESCRIPTION

The following description sets forth numerous exemplary configurations, processes, parameters, and the like. It should be recognized, however, that such description is not intended as a limitation on the scope of the present disclosure, but is instead provided as a description of exemplary embodiments.

The following description relates to processes involving acid-catalyzed conversion of biomass to produce substituted furans, such as halomethylfurfural, hydroxymethylfurfural, and furfural, by using a multiphase reactor.

Acid-Catalyzed Conversion of Biomass

Glycans and heteroglycans in biomass can be converted into substituted furans. In some embodiments, cellulose and hemicellulose in biomass can be converted into halomethylfurfural, hydroxymethylfurfural, and/or furfural in the presence of an acid. Other products, such as levulinic acid and formic acid, may also be produced in the reaction. The acid cleaves the glycosidic bond in glycans and heteroglycans to yield sugar and water by catalytic hydrolysis and dehydration of the cellulose and hemicellulose. The acid then reacts with the sugars to produce substituted furans. In some embodiments, the acid cleaves the glycosidic bond in cellulose and hemicellulose to yield sugar and water by catalytic hydrolysis and dehydration of the cellulose and hemicellulose. The acid then reacts with the sugars to produce halomethylfurfurals.

Figure 1:
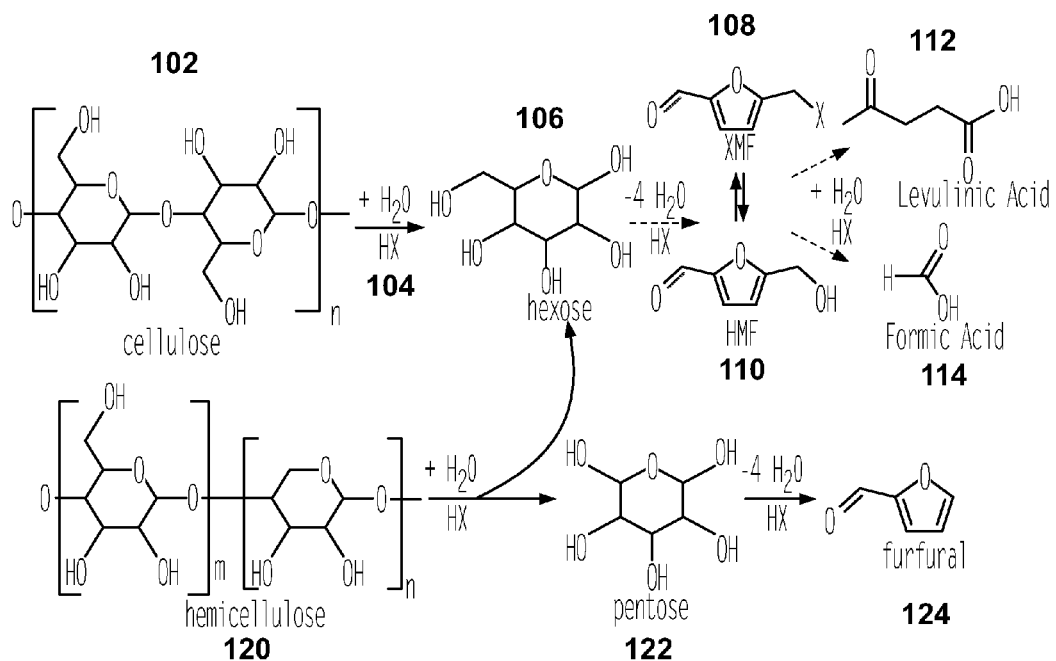
FIG. 1 is an exemplary reaction scheme that shows the conversion of cellulose and hemicellulose into 5-(chloromethyl)furfural, 5-hydroxymethylfurfural, and furfural by acid-catalyzed hydrolysis and dehydration.

With reference to FIG. 1, in an exemplary process, cellulose 102 is hydrolyzed in the presence of a gaseous halogen-based mineral acid 104 to produce hexose 106 (e.g., glucose, fructose), which then undergoes dehydration in the acidic environment to produce halomethylfurfural 108 and hydroxymethylfurfural 110.

Given the acidic reaction conditions, however, halomethylfurfural 108 and hydroxymethylfurfural 110 may rehydrate to produce levulinic acid 112 and formic acid 114. Among the products formed from this exemplary reaction, halomethylfurfurals are the preferred product because they are more reactive intermediates for conversion into biofuels and biodiesel additives and derivative products, compared to the other co-products.

In addition to cellulose as a starting material, hemicellulose in the biomass can also undergo hydrolysis. With reference to FIG. 1, hemicellulose 120 can be hydrolyzed to form hexose 106 and pentose 122 (e.g., arabinose, xylose). Pentose 122 can be converted into furfural 124.

It should be understood that additional components may be added to any of the reactions in the exemplary reaction scheme depicted in FIG. 1. For example, in other exemplary embodiments, a proton donor, a solvent, a desiccant, or any combination thereof may be added to produce halomethylfurfural 108 and hydroxymethylfurfural 110 from cellulose 102 in the presence of a gaseous halogen-based mineral acid 104.

The processes described herein employ various components, including a multiphase reactor, solid feedstock, and a gaseous acid, to carry out the conversion of cellulose and/or hemicellulose to produce substituted furans.

The Multiphase Reactor

A multiphase reactor is a reactor vessel that can be used to carry out chemical reactions in two or more phases (i.e., solid, liquid, gas). The multiphase reactor used in the processes described herein may be a fluidized bed reactor or other multiphase reactors. By using a multiphase reactor for the processes described herein, a single high-pressure, high-temperature operation unit for combined and rapid single-step may be used to directly convert sugars from glycans and heteroglycans into biofuels and chemicals. In some embodiments, the multiphase reactor may be used to directly convert sugars from cellulose and hemicellulose into biofuels and chemicals. Thus, the use of a multiphase reactors in the processes described herein may lead to operation cost-savings since existing methods to produce biofuels and chemicals from cellulose and hemicellulose typically involve two steps: first, producing fermentable sugars from lignocellulose, and then, fermenting these sugars into biofuels and chemicals.

a) Fluidized Bed Reactors

In a fluidized bed reactor, a fluid (either a gas or a liquid) is passed through solid particles at high velocities to suspend the solid particles, causing the solid particles to behave in a suspension. This phenomenon is known as fluidization.

A fluidized bed reactor may offer several advantages. For example, fluidization enables thorough and rapid mixing of the suspended solids around the bed, allowing for uniform heat transfer and uniform mixing, and eliminating hot spots within the reactor mixture. Moreover, thorough and rapid mixing minimizes the need to pretreat biomass to access the cellulose and hemicellulose.

When a gas is used as the fluid in the reactor, high gas phase diffusivities overcome some of the mass transfer barriers. For example, the Schmidt number of gaseous hydrochloric acid is lower than that of aqueous hydrochloric acid, allowing the reaction to proceed at a faster rate. When the reaction is run at high temperatures, the increased diffusivity is further magnified due to low gas phase heat capacity. Thus, the combination of increased diffusivity and high reaction temperatures can significantly reduce reaction times.

Further, the faster reaction rate also allows the use of smaller, more affordable reactors capable of processing the same throughput of material, which may decrease capital costs. Consequently, the size and capacity of handling equipment for the reactors may also be reduced, which may further decrease capital costs. Energy costs may also be lowered with the reduced heat capacity, which contributes to making the processes described herein more economically and commercially feasible. Moreover, increasing throughput as a result of faster reaction rates affords the ability to recycle unreacted materials. By optimizing the reaction rate and recycling unreacted materials, the reactions may be driven to optimal conversion and selectivity, favoring reactions towards the substituted furans (e.g., halomethylfurfural and hydroxymethylfurfural), while minimizing the reactions towards other products, such as levulinic acid and formic acid.

A fluidized bed reactor also allows for continuous operation, which confers a commercial advantage for scaling up reactions compared to batch operations. The solid feed can be continuously introduced into the fluidized bed reactor by using an airlock feed valve. A fluidized bed reactor has the capacity of handling large volumes of biomass with minimal feedstock preparation. For example, the feedstock used in this type of reactor only requires drying and grinding before introduction into the reactor, thereby eliminating the need for expensive enzymatic pretreatments.

b) Other Multiphase Reactors

Other multiphase reactors may be used to achieve thorough and rapid mixing of the solids with gas. For example, plug-flow reactors may be used. Other methods of mixing may also be employed, such as mechanical mixing and gravity. These methods of mixing may be independent of gas flow rates. For example, mechanically-driven method for mixing may be provided by an auger or agitation system.

The Feedstock

The feedstock used in the processes described herein includes biomass. Biomass can be plant material made up of organic compounds relatively high in oxygen, such as carbohydrates, and also contain a wide variety of other organic compounds. Lignocellulosic biomass is a type of biomass that is made up of cellulose and/or hemicellulose bonded to lignin in plant cell walls.

The feedstock may originate from various sources. For example, in some embodiments, the feedstock may originate from waste streams, e.g., municipal wastewater, pulp waste, food processing plant waste, restaurant waste, yard waste, forest waste, biodiesel transesterification waste, and ethanol process waste. In other embodiments, suitable feedstock may include corn stover, rice hulls, rice straw, wheat straw, paper mill effluent, newsprint, municipal solid wastes, wood chips, forest thinings, slash, miscanthus, switchgrass, sorghum, bagasse, manure, wastewater biosolids, green waste, and food/feed processing residues. In yet other embodiments, the feedstock may be fructose or glucose. Any combination of the feedstock described above may also be used as a starting material for the processes described herein.

The processes described herein can handle feedstock that is heterogeneous in nature, without increasing the occurrence of side products, such as alkoxymethylfurfurals that may be formed from cellular debris containing nucleophilic alcohols. The biomass used may have materials such as, for example, particulates, lignin, inorganic salts, and cellular debris. Particulates may include, for example, clays, silica, and humic materials. In some embodiments, the lignin content of the biomass may be less than or equal to about 60%. In some embodiments, inorganic salts may include sulfate or carbonate salts.

The biomass may further include glycans (e.g., cellulose, fructose, glucose, oligomeric starches) as well as fatty acids. It should also be understood, however, that although the processes described herein are well-suited to handling heterogeneous feedstock, pure or relatively pure cellulose and/or hemicellulose may be also used.

In some embodiments, the feedstock contains less than 10%, less than 9%, less than 8%, less than 7%, less than 6%, less than 5%, less than 4%, less than 3%, less than 2%, less than 1% water, less than 0.1%, less than 0.01%, or less than 0.001% (wt/wt basis). In yet other embodiments, the feedstock contains between 1-10%, between 2-10%, between 2-4%, between 1-2%, between 0.01-2%, or between 0.001-2% water (wt/wt basis).

The Gaseous Acid

The acid used in the processes described herein is in a gaseous state. As used herein, the term "gaseous acid" refers to any acid that can go into the gaseous state.

In some embodiments, the gaseous acid is dry. As used herein, the term "dry" refers to a substance with a water content lower than its azeotrope concentration.

In other embodiments, the gaseous acid contains less than 10%, less than 9%, less than 8%, less than 7%, less than 6%, less than 5%, less than 4%, less than 3%, less than 2%, less than 1% water, less than 0.1%, less than 0.01%, or less than 0.001% (wt/wt basis). In yet other embodiments, the gaseous acid contains between 1-10%, between 2-10%, between 2-4%, between 1-2%, between 0.01-2%, or between 0.001-2% water (wt/wt basis). The gaseous acid is undissociated when fed into the multiphase reactor, and dissociates upon adsorption to the glycans and/or heteroglycans in the biomass.

The acid employed may either be halogen-based mineral acids or halogen-based organic acids. In one embodiment, any halogen-based mineral acid may be used. Examples may include hydrochloric acid (HCl), hydrofluoric acid (HF), hydrobromic acid (HBr), and hydroiodic acid (HI). In another embodiment, any halogen-based organic acid that can induce hydration and ring cyclization to form the substituted furans may also be used. In some embodiments, any halogen-based organic acids that can induce hydration and ring cyclization to form the halomethylfurfural may be used. Suitable halogen-based organic acids may include, for example, trifluoroacetic acid (TFA). In certain embodiments, a halogen-based acid may be used.

The concentration of the gaseous acid used in the processes described herein may vary. In some embodiments, the concentration of the gaseous acid is less than or equal to 8.7M. In other embodiments, the concentration of the gaseous acid is less than or equal to 2.4M. In other embodiments, the concentration of the gaseous acid is less than or equal to 0.2M. In other embodiments, the concentration of the gaseous acid is less than or equal to 0.02M. In other embodiments, the concentration of the gaseous acid is between 0.0001M and 8.7M. In other embodiments, the concentration of the gaseous acid is between 2.4M and 8.7M. In other embodiments, the concentration of the gaseous acid is between 0.2M and 2.4M. In other embodiments, the concentration of the gaseous acid is between 0.02M and 0.2M. In other embodiments, the concentration of the gaseous acid is between 0.0001M and 0.02M.

The processes described herein may further include separating the gaseous acid from the reaction mixture using a solid-gas separator, such as for example a cyclone, a filter, or a gravimetric system. Additionally, the processes may further include drying the separated gaseous acid, and returning the dried gaseous acid to the reactor. In some embodiments, drying a substance refers to removing water from a substance so that its water content is lower than its azeotrope concentration. In other embodiments, drying a substance refers to removing water from a substance so that its water content is less than 10%, less than 9%, less than 8%, less than 7%, less than 6%, less than 5%, less than 4%, less than 3%, less than 2%, less than 1% water, less than 0.1%, less than 0.01%, or less than 0.001% (wt/wt basis). In yet other embodiments, drying a substance refers to removing water from a substance so that its water content is between 1-10%, between 2-10%, between 2-4%, between 1-2%, between 0.01-2%, or between 0.001-2% water (wt/wt basis).

The Proton Donor

A proton donor may be added to the reaction mixture. In some embodiments, the proton donor is a Lewis acid. In other embodiments, the proton donor is non-nucleophilic. In yet other embodiments, the proton donor may be soluble in the reaction mixture under the reaction conditions described herein. In yet other embodiments, the proton donor may have a pKa value less than the gaseous acid used in the reaction. The Lewis acid used as the proton donor may complex with the gaseous acid in the reaction to form a superacid. As used herein, a "superacid" is an acid with a pKa less than the pKa of pure sulfuric acid. Any combinations of the proton donors described above may also be used.

In some embodiments, the proton donor may be selected from lithium chloride, sodium chloride, potassium chloride, magnesium chloride, calcium chloride, zinc chloride, aluminum chloride, boron chloride, and any combination thereof. In one embodiment, the proton donor may be calcium chloride, aluminum chloride, or boron chloride. In one embodiment, the proton donor is aluminum chloride, or in the case that multiple proton donors are used, at least one of the proton donors is aluminum chloride.

In some embodiments, the proton donor contains less than 10%, less than 9%, less than 8%, less than 7%, less than 6%, less than 5%, less than 4%, less than 3%, less than 2%, less than 1% water, less than 0.1%, less than 0.01%, or less than 0.001% (wt/wt basis). In other embodiments, the proton donor contains between 1-10%, between 2-10%, between 2-4%, between 1-2%, between 0.01-2%, or between 0.001-2% water (wt/wt basis).

The Solvent

A solvent may be added to the reaction mixture. Suitable solvents may include, for example, dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, or supercritical carbon dioxide. In one embodiment, the solvent is dichloromethane or dichloroethane. Any combination of the solvents described above may also be used In some embodiments, the solvent is dry. In other embodiments, the solvent contains less than 10%, less than 9%, less than 8%, less than 7%, less than 6%, less than 5%, less than 4%, less than 3%, less than 2%, less than 1% water, less than 0.1%, less than 0.01%, or less than 0.001% (wt/wt basis). In yet other embodiments, the solvent contains between 1-10%, between 2-10%, between 2-4%, between 1-2%, between 0.01-2%, or between 0.001-2% water (wt/wt basis).

Producing Substituted Furans (e.g., Halomethylfurfural, Hydroxymethylfurfural, and Furfural)

The processes described herein may be employed to produce substituted furans from biomass containing glycans and/or heteroglycans. In some embodiments, the processes described herein may be employed to produce halomethylfurfural, hydroxymethylfurfural, and/or furfural from biomass containing cellulose and/or hemicellulose. Other co-products may include levulinic acid, formic acid, and optionally substituted alkylfurfural (e.g., methylfurfural).

a) Feeding in the Biomass and Gaseous Acid

Figure 2:
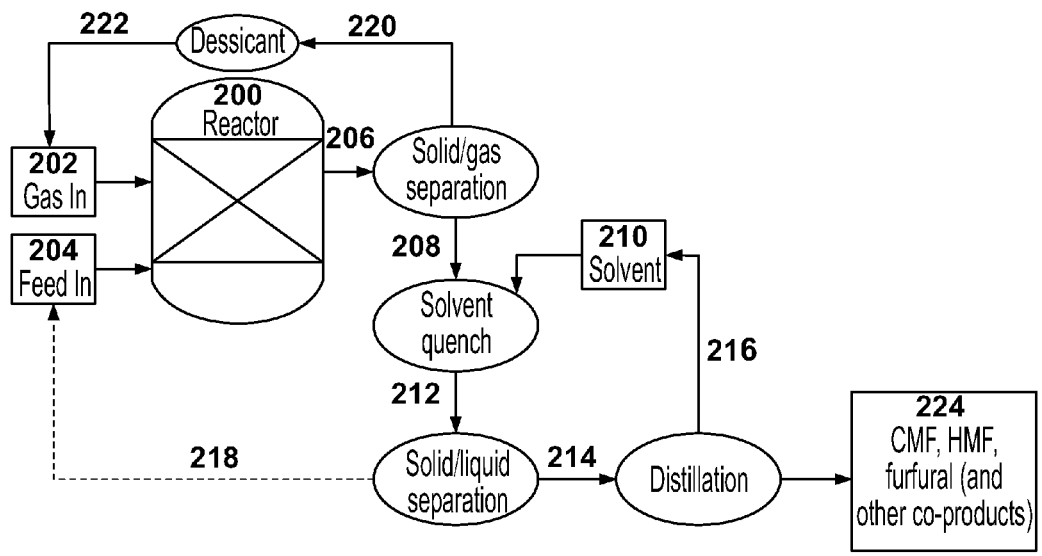
FIG. 2 depicts a block diagram for an exemplary process of producing substituted furans (e.g., halomethylfurfural, hydroxymethylfurfural, and furfural) in a multiphase reactor, in which the dotted lines represent optional inputs or steps.

With reference to FIG. 2, in one embodiment, gaseous hydrochloric acid (HCl) 202 and solid biomass 204 is continuously fed into fluidized bed reactor 200. In this exemplary embodiment, hydrochloric acid (HCl) 202 has less than 0.001% by weight of water. In other exemplary embodiments, the amount of the gaseous acid may have different amounts of water, for example, less than 10% by weight of water. In reactor 200, the gaseous acid and feedstock is fed into the side of the reactor. It should be recognized, however, that any combination of side inputs, bottom inputs, and top inputs may be used, depending on the type of multiphase reactor used.

Gaseous HCl 202 is fed into reactor 200 at high velocities to create an upward-flowing stream of gas that suspends solid biomass 204. Fluidization allows for uniform mixing between the acid and biomass. Solid biomass 204 is hydrolyzed and dehydrated in the presence of gaseous HCl 202 to yield chloromethylfurfural, hydroxymethylfurfural, and furfural.

b) Product Selectivity

As discussed above, the substituted furans may rehydrate in the acidic reaction conditions to produce levulinic acid and formic acid, which are often considered lower-valued products in the context of biofuel production. In some embodiments, halomethylfurfural and hydroxymethylfurfural may rehydrate in the acidic reaction conditions to produce levulinic acid and formic acid. Thus, this possibility of rehydration presents a challenge to commercial use of the processes for biofuel production.

The processes described herein favor the formation of substituted furans (e.g., halomethylfurfural and hydroxymethylfurfural) over levulinic acid and formic acid. Without wishing to be bound by any theory, a reaction at higher temperatures may be driving dehydration faster than rehydration. As observed based on the measured activation energy and other kinetic parameters, the hot gas phase system described herein yields better product selectivity. The rate of hexose dehydration to substituted furans (e.g., halomethylfurfural) may be more sensitive to temperature than the subsequent rehydration to levulinic acid and formic acid, whereas the rate of rehydration may be more sensitive to acid concentration than may be the production of substituted furans (e.g., halomethylfurfural). Running the reaction at low acid concentrations and at high temperatures may drive product selectivity, favoring the substituted furans (e.g., halomethylfurfural and hydroxymethylfurfural) over levulinic acid and formic acid. These reaction conditions may be achieved in a gas phase system, as described herein.

c) Reaction Conditions

The reactor temperature range may be between the temperature at which little to no dehydration of glucose would occur and the temperature at which pyrolysis starts to take over. In some embodiments, the temperature in the multiphase reactor is between 50° C. and 500° C. In other embodiments, the temperature in the multiphase reactor is between 100° C. and 400° C. In other embodiments, the temperature in the multiphase reactor is between 100° C. and 350° C. In yet other embodiments, the temperature in the multiphase reactor is between 150° C. and 300° C. In yet other embodiments, the temperature in the multiphase reactor is between 200° C. and 250° C.

The higher reaction temperatures used in the processes described herein increases the reaction yield because lignin may trap gaseous acids at low temperatures. When trapped in lignin, the acid is less available to react with the biomass; however, this inefficiency may be mitigated at higher reaction temperatures because heat drives acid from the lignin and prevents the acid from binding to the lignin. Reduced carry-over of acid in lignin also creates process cost-savings because less acid is lost for use as a solvent and/or catalyst and less acid is needed to replenish the system. Moreover, running the processes at higher temperatures may reduce the formation of poly-halogenated phenyls.

The reactor pressure may range between 0.001 atm to 350 atm. In some embodiments, the processed described herein is performed in a vacuum. In other embodiments, the pressure in the multiphase reactor is between 0.001 atm and 200 atm. In other embodiments, the pressure in the multiphase reactor is between 0.001 atm and 100 atm. In yet other embodiments, the pressure in the multiphase reactor is between 0.001 atm and 10 atm. In yet other embodiments, the pressure in the multiphase reactor is between 1 atm and 50 atm. In yet other embodiments, the pressure in the multiphase reactor is between 1 atm and 10 atm.

In some embodiments, the reaction mixture inside the multiphase reactor has less than 10%, less than 9%, less than 8%, less than 7%, less than 6%, less than 5%, less than 4%, less than 3%, less than 2%, less than 1%, less than 0.05%, less than 0.01%, less than 0.005%, or less than 0.001% by weight of water. In certain embodiments, the reaction mixture inside the multiphase reactor has between 1% and 10%, between 2% and 10%, between 2% and 4%, between 1% and 5%, between 1% and 2%, between 0.1% and 2%, between 0.01% and 2%, or between 0.001% and 2% water (wt/wt basis).

To achieve the water content in the reaction mixture described above, reactants and/or reagents (e.g., feedstock, gaseous acid, proton donor and/or solvent) with less than 10% by weight of water may be used. Desiccants may also be added to the multiphase reactor. For example, in some embodiments, molecular sieves may be added to the multiphase reactor to sequester water from the reaction mixture. In certain embodiments, reactants and/or reagents with less than 10% by weight of water and desiccants may be used to control the water content of the reaction mixture.

d) Solid/Gas Separation

When the gas and the solids reach the top of reactor 200 (i.e., the end of the reactor), crude reaction mixture 206 exits due to the pressure difference inside and outside the reactor. It should be recognized, however, in reactor systems that are not driven by pressure, movement of the particular matter solids and their exit from the reactor may be driven by gravity and/or mechanical means, e.g., auger systems and/or agitation.

On exit, crude reaction mixture 206 is separated into gaseous HCl 220 and solid mixture 208 containing chloromethylfurfural. It should be understood that the solid mixture may include halomethylfurfural (corresponding to the acid employed), hydroxymethylfurfural, and furfural. Any solid-gas separators known in the art may be used, for example, a cyclone, a filter, or a gravimetric system. Any combination of the solid-gas separators described above may also be used.

Gaseous HCl 220 is then passed through a desiccant to remove any water. The use of a desiccant in the processes described herein presents a cost advantage over acid separation by azeotrope shifting, which is energy intensive and expensive. Rather than relying on phase changes for separation, which may lead to azeotropic effects in aqueous acid solutions, the use of a desiccant allows water to change its affinity for gaseous acid to the desiccant material, enabling more efficient separation.

Dried gaseous HCl 222 is returned to reactor 200. Thus, the acid can be recaptured and recycled back into the system.

e) Solid/Liquid Separation

Solid mixture 208 is combined with solvent 210 to drive the reaction equilibrium towards chloromethylfurfural and hydroxymethylfurfural. Combining solvent 210 with solid mixture 208 produces mixture 212, which contains a solution of the products (e.g., chloromethylfurfural, hydroxymethylfurfural, and furfural) and remaining solids, which contain unreacted starting materials. The components of the unreacted starting materials may include, for example, lignin, grit, minerals, and salts. Unreacted cellulose and hemicellulose may also be present.

Any solvent known in the art suitable to solubilize the substituted furans may be used. Suitable solvents may include, for example, dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, or supercritical carbon dioxide. Any combinations of the solvents described above may also be used.

Any solid-liquid separation methods known in the art, such as a filter or membrane system, can be employed to separate mixture 212 into solution 214 (containing the products), and remaining solids 218 (containing unreacted starting materials). Remaining solids 218 can be optionally recycled and fed back into reactor 200, as shown in FIG. 2. This optional solids recycling step can improve overall reaction yield.

f) Isolating Reaction Products

To isolate reaction products 224, solution 214 undergoes distillation or any other standard separation methods known in the art. Distillation produces separated solvent 216, which may be recycled in the solvent quench, as depicted in FIG. 2. Reaction products 224 collected from the distillation may include substituted furans (e.g., halomethylfurfural, hydroxymethylfurfural, furfural), levulinic acid, and formic acid.

In other embodiments, the isolated substituted furans can be further processed into other furanic derivatives for biofuels, diesel additives, or plastics. In some embodiments, the isolated halomethylfurfural and hydroxymethylfurfural can be further processed into other furanic derivatives for biofuels, diesel additives, or plastics. For example, chloromethylfurfural may be converted into dimethylfuran and ethoxymethylfurfural.

In yet other embodiments, the isolated levulinic acid can be used to in applications that may include, for example, cleaning solvents, coupling agents in liquid formulations, plasticizers, polyols for polyurethane materials, polyester thermosets, thermoplastics, agricultural chemicals, polymer precursors and plastics, synthetic rubbers, pharmaceutical intermediates, photosensitizers, precursor to other chemical commodities, and in cigarettes.

As used herein, the term "about" refers to an approximation of a stated value within an acceptable range. Preferably, the range is +/−10% of the stated value.

EXAMPLES

The following Examples are merely illustrative and are not meant to limit any aspects of the present disclosure in any way.

Example 1

Preparation of 5-(chloromethyl)furfural, 5-(hydroxymethyl)furfural, and Furfural from Lignocellulosic Biomass Lignocellulosic biomass originating from municipal wastewater from Davis (CA) is obtained and fed through a side-input into a 2000-L fluidized bed reactor at a rate of 50 kg/minute. Gaseous hydrochloric acid is fed through another side-input into the reactor at a rate of 4,000 L/min. The temperature inside the reactor is approximately 220° C., and the pressure inside the reactor is approximately 15 atm.

Fluidization occurs inside the reactor, allowing for thorough and uniform mixing of the sludge and gaseous acid. After two minute residence times, the crude reaction mixture of gas and solids reach the top of the reactor, and exit the reactor due to the pressure difference inside (about 15 atm) and outside of the reactor (about 4 atm). As the gas and solids leave the reactor, the crude reaction mixture is separated using a cyclone into gaseous hydrochloric acid and a solid/liquid mixture. A sample of the solid mixture is obtained and analyzed by liquid chromatography-mass spectrometry (LCMS). The solid mixture contains 5-(chloromethyl)furfural, 5-(hydroxymethyl)furfural, and furfural. Additionally, some amounts of levulinic acid and formic acid are observed in the reaction mixture.

The gaseous hydrochloric acid is passed through a desiccant to remove water. This dried gaseous hydrochloric acid is fed back into the fluidized bed reactor.

The solid/liquid mixture is mixed in line with dichloromethane to produce a mixture containing both solids, and an organic solution. This mixture is then filtered. Samples of the retentate solids and the permeate solution are obtained and analyzed by LCMS. The solution permeate contains 5-(chloromethyl)furfural, 5-(hydroxymethyl)furfural, and furfural.

The solution is transferred to a distillation apparatus to isolate the reaction products. The fractions are collected and analyzed by LCMS. 5-(chloromethyl)furfural, 5-(hydroxymethyl)furfural, and furfural are obtained in high purity. The reaction also produces small quantities of levulinic acid and formic acid.

Example 2

Production of 5-(chloromethyl)furfural (CMF) from Fructose

To a clean, dry 350 ml pressure-sealed round bottomed flask equipped with a magnetic stir bar was added granulated fructose (0.75 g, 4.16 mmol). The flask was then placed in an inert argon atmosphere and dry calcium chloride (5.6 g, 50.4 mmol) and aluminum trichloride (0.119 g, 0.832 mmol) were added and the solids suspended in 1,2-dichloroethane (75 ml). The reaction mixture was removed from the inert atmosphere and gaseous hydrochloric acid (0 wt % water) was bubbled into the solution until gas began to fume from the flask. The flask was then sealed and placed in a preheated oil bath set to 85° C. and allowed to stir for 1 hour. The reaction mixture was then allowed to cool to room temperature. The solids were filtered through filter paper, and diluted to 100 mL of solvent. Volumetric analysis using a CMF flame ionization detector (FID)-standard curve indicated a 2.1 mg/ml concentration of CMF. The reaction yielded a total of 210 mg of CMF (35% yield).

What is claimed is:

1. A method for producing a hydroxymethylfurfural in a gas-solid phase reactor, the method comprising:
   feeding solid feedstock into a gas-solid phase reactor, wherein the solid feedstock comprises biomass or sugar, or any combination thereof;
   feeding gaseous acid into the gas-solid phase reactor, wherein the gaseous acid has less than about 10% by weight of water;
   mixing the solid feedstock and the gaseous acid to form a reaction mixture;
   adding lithium chloride, sodium chloride, potassium chloride, magnesium chloride, calcium chloride, zinc chloride, aluminum chloride, or boron chloride, or any combination thereof, to the reaction mixture; and
   producing a hydroxymethylfurfural from at least a portion of the solid feedstock and at least a portion of the gaseous acid in the reaction mixture.

2. The method of claim 1, wherein at least a portion of the gaseous acid in the reaction mixture is unreacted gaseous acid, and wherein the unreacted gaseous acid comprises water, and the method further comprises:
   separating the unreacted gaseous acid from the reaction mixture using a solid-gas separator; and
   drying the separated unreacted gaseous acid to remove at least a portion of the water in the separated unreacted gaseous acid.

3. The method of claim 2, further comprising feeding the dried separated unreacted gaseous acid into the gas-solid phase reactor.

4. The method of claim 1, wherein at least a portion of the gaseous acid in the reaction mixture is unreacted gaseous acid, or at least a portion of the solid feedstock in the reaction mixture is unreacted solid feedstock, or a combination thereof, and the method further comprises:
   separating the hydroxymethylfurfural produced from the unreacted gaseous acid or the unreacted solid feedstock, or a combination thereof, using a solvent, wherein the solvent solubilizes at least a portion of the hydroxymethylfurfural.

5. The method of claim 4, wherein the solvent is selected from the group consisting of dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, and any combination thereof.

6. The method of claim 1, wherein the gas-solid phase reactor is a fluidized bed reactor.

7. The method of claim 1, wherein the gaseous acid is a halogen-based mineral acid or a halogen-based organic acid.

8. The method of claim 1, wherein the gaseous acid is hydrochloric acid.

9. The method of claim 1, wherein the biomass comprises glycans.

10. The method of claim 1, wherein the biomass comprises heteroglycans.

11. The method of claim 1, wherein the hydroxymethylfurfural is 5-(hydroxymethyl)furfural.

12. A method for producing a hydroxymethylfurfural in a gas-solid phase reactor, the method comprising:
   feeding solid feedstock and gaseous acid into a gas-solid phase reactor, wherein the solid feedstock comprises biomass or sugar, or any combination thereof;
   mixing the solid feedstock and the gaseous acid in the presence of lithium chloride, sodium chloride, potassium chloride, magnesium chloride, calcium chloride, zinc chloride, aluminum chloride, or boron chloride, or any combination thereof to form a reaction mixture, under conditions suitable to produce a hydroxymethylfurfural; and
   producing a hydroxymethylfurfural from at least a portion of the solid feedstock and at least a portion of the gaseous acid in the reaction mixture, wherein the reaction mixture has less than 10% by weight of water.

13. The method of claim 12, wherein at least a portion of the gaseous acid in the reaction mixture is unreacted gaseous acid, and wherein the unreacted gaseous acid comprises water, and the method further comprises:
   separating the unreacted gaseous acid from the reaction mixture using a solid-gas separator; and
   drying the separated unreacted gaseous acid to remove at least a portion of the water in the separated unreacted gaseous acid.

14. The method of claim 13, further comprising feeding the dried separated unreacted gaseous acid into the gas-solid phase reactor.

15. The method of claim 12, wherein the gaseous acid is gaseous hydrochloric acid.

16. The method of claim 12, wherein the gaseous acid has less than 10% by weight of water.

17. The method of claim 12, wherein the hydroxymethylfurfural is 5-(hydroxymethyl)furfural.

18. The method of claim 12, wherein the gas-solid phase reactor is a fluidized bed reactor.

19. The method of claim 12, wherein the biomass comprises glycans.

20. The method of claim 12, wherein the biomass comprises heteroglycans.

21. A method for producing a hydroxymethylfurfural in a gas-solid phase reactor, the method comprising:
   feeding solid feedstock into a gas-solid phase reactor, wherein the solid feedstock comprises biomass or sugar, or any combination thereof;
   feeding gaseous acid into the gas-solid phase reactor, wherein the gaseous acid has less than about 10% by weight of water;
   mixing the solid feedstock and the gaseous acid to form a reaction mixture;
   producing a hydroxymethylfurfural from at least a portion of the solid feedstock and at least a portion of the gaseous acid in the reaction mixture, wherein at least a portion of the gaseous acid in the reaction mixture is unreacted gaseous acid, or at least a portion of the solid feedstock in the reaction mixture is unreacted solid feedstock, or a combination thereof; and
   separating the hydroxymethylfurfural produced from the unreacted gaseous acid or the unreacted solid feedstock, or a combination thereof, using a solvent, wherein the solvent solubilizes at least a portion of the hydroxymethylfurfural.

22. The method of claim 21, wherein the solvent is selected from the group consisting of dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, and any combination thereof.

23. The method of claim 21, wherein the unreacted gaseous acid comprises water, and the method further comprises:
   separating the unreacted gaseous acid from the reaction mixture using a solid-gas separator; and
   drying the separated unreacted gaseous acid to remove at least a portion of the water in the separated unreacted gaseous acid.

24. The method of claim 23, further comprising feeding the dried separated unreacted gaseous acid into the gas-solid phase reactor.

25. The method of claim 21, wherein the gas-solid phase reactor is a fluidized bed reactor.

26. The method of claim 21, wherein the gaseous acid is a halogen-based mineral acid or a halogen-based organic acid.

27. The method of claim 21, wherein the gaseous acid is hydrochloric acid.

28. The method of claim 21, wherein the biomass comprises glycans.

29. The method of claim 21, wherein the biomass comprises heteroglycans.

30. The method of claim 21, wherein the hydroxymethylfurfural is 5-(hydroxymethyl)furfural.

31. A method for producing a hydroxymethylfurfural in a gas-solid phase reactor, the method comprising:
feeding solid feedstock and gaseous acid into a gas-solid phase reactor, wherein the solid feedstock comprises biomass or sugar, or any combination thereof;
mixing the solid feedstock and the gaseous acid to form a reaction mixture, under conditions suitable to produce a hydroxymethylfurfural;
producing a hydroxymethylfurfural from at least a portion of the solid feedstock and at least a portion of the gaseous acid in the reaction mixture, wherein the reaction mixture has less than 10% by weight of water and wherein at least a portion of the gaseous acid in the reaction mixture is unreacted gaseous acid, or at least a portion of the solid feedstock in the reaction mixture is unreacted solid feedstock, or a combination thereof; and
separating the hydroxymethylfurfural produced from the unreacted gaseous acid or the unreacted solid feedstock, or a combination thereof, using a solvent, wherein the solvent solubilizes at least a portion of the hydroxymethylfurfural.

32. The method of claim 31, wherein the solvent is selected from the group consisting of dichloromethane, ethylacetate, hexane, cyclohexane, benzene, toluene, diethyl ether, tetrahydrofuran, acetone, dimethyl formamide, dimethyl sulfoxide, acetonitrile, methanol, ethanol, isopropanol, n-propanol, n-butanol, chloroform, dichloroethane, trichloroethane, furfural, furfuryl alcohol, supercritical carbon dioxide, and any combination thereof.

33. The method of claim 31, wherein at least a portion of the gaseous acid in the reaction mixture is unreacted gaseous acid, and wherein the unreacted gaseous acid comprises water, and the method further comprises:
separating the unreacted gaseous acid from the reaction mixture using a solid-gas separator; and
drying the separated unreacted gaseous acid to remove at least a portion of the water in the separated unreacted gaseous acid.

34. The method of claim 31, further comprising feeding the dried separated unreacted gaseous acid into the gas-solid phase reactor.

35. The method of claim 31, wherein the gaseous acid is gaseous hydrochloric acid.

36. The method of claim 31, wherein the gaseous acid has less than 10% by weight of water.

37. The method of claim 31, wherein the hydroxymethylfurfural is 5-(hydroxymethyl)furfural.

38. The method of claim 31, wherein the gas-solid phase reactor is a fluidized bed reactor.

39. The method of claim 31, wherein the biomass comprises glycans.

40. The method of claim 31, wherein the biomass comprises heteroglycans.

* * * * *